United States Patent
Rowland

(10) Patent No.: US 9,890,346 B2
(45) Date of Patent: Feb. 13, 2018

(54) SELECTIVE ALKYLATION METHOD FOR PRODUCING P, P'-DI-ALKYLATED DIPHENYLAMINE ANTIOXIDANTS

(71) Applicant: Chemtura Corporation, Middlebury, CT (US)

(72) Inventor: Robert G Rowland, Woodbridge, CT (US)

(73) Assignee: LANXESS Solutions US Inc., Middlebury, CT (US)

( * ) Notice: Subject to any disclaimer, the term of this patent is extended or adjusted under 35 U.S.C. 154(b) by 0 days.

(21) Appl. No.: 14/754,383

(22) Filed: Jun. 29, 2015

(65) Prior Publication Data

US 2016/0017252 A1 Jan. 21, 2016

Related U.S. Application Data

(60) Provisional application No. 62/026,787, filed on Jul. 21, 2014.

(51) Int. Cl.
| | |
|---|---|
| C10M 133/12 | (2006.01) |
| C07C 209/68 | (2006.01) |
| C10M 177/00 | (2006.01) |
| C07C 211/55 | (2006.01) |

(52) U.S. Cl.
CPC ......... *C10M 133/12* (2013.01); *C07C 209/68* (2013.01); *C07C 211/55* (2013.01); *C10M 177/00* (2013.01); *C10M 2215/064* (2013.01); *C10N 2230/10* (2013.01)

(58) Field of Classification Search
None
See application file for complete search history.

(56) References Cited

U.S. PATENT DOCUMENTS

| | | |
|---|---|---|
| 4,163,757 A | 8/1979 | D'Sidocky |
| 5,186,852 A | 2/1993 | Ishida et al. |
| 6,204,412 B1 | 3/2001 | Lai |
| 6,315,925 B1 | 11/2001 | Aebli et al. |
| 6,355,839 B1 | 3/2002 | Onopchenko |
| 7,145,038 B1 | 12/2006 | Hobbs |
| 2006/0205981 A1 | 9/2006 | Andruskova et al. |
| 2008/0161216 A1 | 7/2008 | Simard |

OTHER PUBLICATIONS

PCT International Preliminary Report on Patentability dated Feb. 2, 2017 from corresponding Application No. PCT/US2015/041071, 8 pages.

*Primary Examiner* — Clinton A Brooks
(74) *Attorney, Agent, or Firm* — Dilworth IP LLC

(57) ABSTRACT

Liquid diphenylamine compositions comprising predominately p,p'-di-alkylated diphenylamines and low amounts of mono-alkylated diphenylamines are prepared by adding an olefin to a mixture comprising mono-alkylated diphenylamines, di-alkylated diphenylamines, Lewis acid catalyst and an amount of another olefin sufficient to suppress dealkylation of the alkylated diphenylamines.

11 Claims, No Drawings

SELECTIVE ALKYLATION METHOD FOR PRODUCING P, P'-DI-ALKYLATED DIPHENYLAMINE ANTIOXIDANTS

This application claims benefit under 35 USC 119(e) of U.S. Provisional Application No. 62/026,787, filed Jul. 21, 2014, the disclosure of which is incorporated herein by reference.

Liquid diphenylamine compositions comprising predominately p, p'-di-alkylated diphenylamines and very low amounts of mono-alkylated diphenylamines are prepared by adding a second olefin to a mixture comprising mono- and di-alkylated diphenylamines, a Lewis acid catalyst and a first olefin in an amount sufficient to suppress dealkylation of the alkylated diphenylamines.

BACKGROUND

Lubricants are often used in demanding environments where degradation of the lubricant base stock can lead to catastrophic results; and where such degradation is accelerated by high temperatures, extreme wear conditions, acidic or other corrosive conditions, etc. For example, automobile engines require periodic oil changes to replace degraded engine lubricant in order to protect against undue wear and engine damage.

Alkylated diphenylamines (ADPAs) are antioxidants widely used to prevent degradation and maintain the performance of modern engine oils found in gasoline and diesel engines for cars and trucks. Motor oil drain intervals have been significantly extended in recent years through the use of modern antioxidant formulations, coupled with improved base-stocks. Extending drain intervals conserves oil, reduces used oil and filter waste, and helps reduce the illegal disposal of used oil.

When selecting an ADPA antioxidant component for use a number of performance, safety and environmental concerns must be addressed. For example, diphenylamine itself has good antioxidant activity but it has long been known to be a sensitizer and its presence is typically kept to a minimum, e.g., less than 1% of any ADPA antioxidant. Further, diphenylamines substituted with essentially hydrocarbyl groups are more soluble in lubricating oil and the higher molecular weight reduces volatility. Increasing alkylation also helps to solubilize polar materials that form by oligomerization of spent oxidized amines reducing deposits, sludge and varnish.

On the other hand, the antioxidant activity of ADPAs is dependent on the concentration of nitrogen provided and is thus inversely proportional to molecular weight and excessive alkylation or very large alkyl groups should be avoided.

For an ADPA with a molecular weight of up to about 400 to 600 Daltons, other factors can be as important as nitrogen content. For example, alkylation of the aromatic ring at the para-position relative to the nitrogen is preferred as ortho-alkylation diminishes the activity of the amino group. Orthoalkylation, and ortho, para-alkylation should be minimized as much as possible. Since tri-alkylation of DPA overwhelmingly requires that one ring is ortho, parasubstituted, tri-alkylation is by definition undesirable.

When formulating a lubricant, liquid components, i.e., liquid at room temperature, e.g., 25° C., are typically preferred, as they are easier than solids to handle in the blending process. Liquids are also less likely to cause pour-point, gelling, or filter-clogging problems by crystallizing out of an oil than an additive that is itself a crystalline solid. Friedel-Crafts alkylation of diphenylamine is an equilibrium driven process and commercial ADPAs are often mixtures containing varying proportions of mono-, di-, and tri-alkylated diphenylamines, and tend to be liquid provided that certain ratio of the various products are obtained.

Also, as disclosed in U.S. Pat. No. 6,204,412, symmetrically disubstituted diphenylamines typically increase the melting point of the alkylated diphenylamine composition and can, in sufficient amounts, lead to a solid alkylated diphenylamine composition rather than a liquid. For example, a composition with 25 wt % or more dioctyldiphenylamine, obtained e.g., by reaction between diphenylamine and diisobutylene, is typically solid at room temperature. Thus, a balance must be found between the components of an ADPA mixture to ensure the proper product form.

There are processes in the art designed to provide an alkylated diphenylamine composition that is liquid at room temperature and contains a minimum amount of non-alkylated diphenylamine. For example, U.S. Pat. No. 6,204,412 discloses a method of manufacturing an alkylated diphenylamine composition comprising no more than 3 wt % unsubstituted diphenylamine, comprising steps of (a) reacting unsubstituted diphenylamine and at least one olefin comprising diisobutylene or other select linear alpha-olefins in the presence of a clay catalyst to form a reactive composition; and (b) adding a second olefin composition to the reactive composition to react with the reactive composition and generate an alkylated diphenylamine composition comprising no more than 3 wt % unsubstituted diphenylamine, wherein at least a portion of the second olefin composition is added to the reactive composition prior to forming 50 wt % mono-alkylated diphenylamine in the reaction mixture. The second olefin composition generally comprises isobutylene, styrene, or alpha-methylstyrene, which are more reactive with unsubstituted diphenylamine than the olefin of step (a).

U.S. Pat. No. 6,355,839 discloses a single step process for preparation of an alkylated diphenylamine antioxidant which comprises alkylating diphenylamine with polyisobutylene in the presence of a clay catalyst, wherein the polyisobutylene has an average molecular weight in the range of 120 to 600 and wherein the polyisobutylene contains at least 25% methylvinylidene isomer.

U.S. Pat. No. 6,315,925 provides a mixture of nonylated diphenylamines consisting essentially of, as measured by gas chromatography, a) from 68% to 78% by area dinonyldiphenylamine; b) from 20 to 30% by area nonyldiphenylamine; c) from 1.0 to 3.5% by area trinonyldiphenylamine; and d) from 0.1 to 1.0% by area diphenylamine; and a process for the preparation thereof by using acid catalysts in small quantities.

Methods are known that provide liquid ADPA mixtures with low non-alkylated diphenylamine content. Typically these mixtures comprise a significant amount, i.e., 20 wt % or more of mono-alkylated diphenylamine. However, approaches useful in reducing the amount of non-alkylated DPA in these mono-alkylated DPA rich diphenylamine compositions can be surprisingly unsuccessful and/or commercially unfeasible when applied to the reduction of mono-alkylated DPA concentrations in preparing liquid di-alkylated DPA compositions that are very low in mono-alkylated DPA. For example, attempts to convert mono-nonylated para-diphenylamine to a di-alkylated diphenylamine by reaction with diisobutylene resulted in the loss of nonyl groups, which can be replaced by alkylation with octyl groups forming the less desired t-octyl-diphenylamine.

Reactions of mono-alkylated DPA with styrene or alpha-methylstyrene are potentially problematic due to environmental concerns.

The present invention provides liquid compositions with high amounts of di-alkylated DPA and low amounts of mono-alkylated DPA and a process for conveniently preparing said compositions. It is believed that the antioxidant compositions provided by the invention will have advantages in handling, compatibility and performance over other alkylated DPA compositions in many commercial applications.

SUMMARY OF THE INVENTION

A liquid alkylated diphenylamine composition comprising, based on the on the total weight of substituted and unsubstituted diphenylamine compounds in the liquid alkylated diphenylamine composition, from about 70% to about 100%, typically about 80% to about 100%, by weight of one or more di-alkylated diphenylamines, which di-alkylated diphenylamines are predominately, e.g., over 50%, 4,4'-di-alkylated diphenylamines, and about 15% by weight or less, e.g., about 10 wt % or less and in some embodiment about 5 wt % or less, of mono-alkylated diphenylamines, wherein the alkyl groups are selected from $C_{4-24}$ alkyl groups and wherein at least one alkyl group of at least one of the one or more di-alkylated diphenylamines contains from 8 to 24 carbon atoms, is obtained by a process wherein a reaction mixture comprising mono-alkylated diphenylamine, di-alkylated diphenylamine, Lewis acid catalyst and an olefin, also referred to herein as a "first olefin", present in a quantity sufficient to suppress dealkylation is reacted with a second olefin in sufficient quantity to reduce the amount of mono-alkylated diphenylamine to about 15 wt % or less, e.g., about 10 wt % or less often about 5 wt % or less.

The diphenylamine compositions of the invention are liquid at ~25° C., soluble or miscible in many lubricants and polymers, and provide excellent antioxidant activity.

The olefin present in a quantity sufficient to suppress dealkylation is referred to herein as a "first olefin" and is a single olefin or a mixture of olefins that is known by one skilled in the art as capable of producing the mixture of mono-alkylated diphenylamine and di-alkylated diphenylamine of the above reaction mixture when reacted with diphenylamine in the presence of an acidic catalyst. For example, a mixture of mono-octyl and di-octyl diphenylamines can be prepared from diphenylamine by alkylation with diisobutylene. Diisobutylene would therefore be one obvious choice for "first olefin" when further alkylating the mixture according to the process of the invention. As it is possible the first olefin comprises more than a single olefin, the term "first olefinic agent" is also used to refer to the first olefin.

The "second olefin" or "second olefinic agent" is any olefin or mixture of olefins that is chemically different from that of the "first olefin" or "first olefinic agent", either in the number of carbons, extent or location of branching, position of carbon/carbon double bond, olefin substitution, etc., that is used to further alkylate the mixture of mono-alkylated diphenylamine and di-alkylated diphenylamine according to the present process. In certain embodiments the "second olefinic agent" may comprise a mixture of the same compounds found in the first olefinic agent in a different compositional ratio.

In one embodiment, the process above comprises a further preliminary step in which the mono-alkylated and di-alkylated diphenylamines of the reaction mixture is produced. For example, in one embodiment the liquid alkylated diphenylamine composition is obtained by a process comprising:
a) alkylating diphenylamine and/or a mono-alkylated diphenylamine with a first olefinic agent in the presence of a Lewis acid catalyst to produce a reaction mixture comprising mono- and di-alkylated diphenylamines, wherein di-alkylated diphenyl amines are present in a larger quantity than mono-alkylated diphenylamines,
b) adding additional first olefinic agent sufficient to suppress dealkylation, and
c) adding a second olefinic agent in sufficient quantity to reduce the amount of mono-alkylated diphenylamine to about 15 wt % or less, e.g., about 10 wt % or less or about 5 wt % or less, of all substituted and unsubstituted diphenylamine compounds in the mixture, wherein steps b) and c) may be performed sequentially or together.

DESCRIPTION OF THE INVENTION

The liquid alkylated diphenylamine compositions of the present invention comprise diphenylamine compounds, wherein at least 70 wt %, typically 80 wt % or more, of all diphenylamine compounds in the composition are di-alkylated, at most 15 wt %, often 10 wt % or less or 5 wt % or less, of all diphenylamine compounds in the composition are mono-alkylated, less than 2%, typically less than 1%, of all diphenylamine compounds in the composition is unsubstituted diphenylamine, and over 50%, often over 60%, of all di-alkylated diphenylamine compounds are 4,4'-di-alkylated diphenylamines.

In many embodiments, at least 75 wt %, 80 wt %, 85 wt %, 90 wt %, 95 wt % or more of all diphenylamine compounds in the composition are di-alkylated, and in many embodiments at least 55%, 60%, 65%, 70%, 75%, 80%, 85%, 90% or more of the di-alkylated diphenylamine compounds are 4,4'-di-alkylated compounds. For example, in one particular embodiment, 80 wt % or more of all diphenylamine compounds are di-alkylated diphenylamines wherein 80% or more of all di-alkylated diphenylamine compounds are 4,4'-di-alkylated diphenylamines, i.e., a composition wherein at least 64% by weight of all diphenylamine compounds are 4,4'-di-alkylated diphenylamine compounds.

In many embodiments the liquid alkylated diphenylamine composition of the invention comprises, e.g., from about 70% to 100% by weight, e.g., from about 80% to 100% by weight, based on the on the total weight of substituted and unsubstituted diphenylamine compounds, of one or more di-alkylated diphenylamines of formula (I) and (Ia)

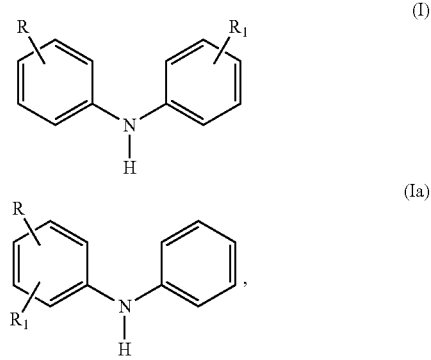

wherein R is $C_{8-24}$ alkyl, and $R_1$ is $C_{4-24}$ alkyl, often $R_1$ is $C_{4-12}$ alkyl and in some embodiments R is selected from $C_{8-12}$ alkyl. More than one R group and/or more than one $R_1$ group may be present in the product mixture and often at least a portion of the composition will comprise one or more compounds wherein R and $R_1$ are the same $C_{8-24}$ or $C_{8-12}$ alkyl group. Compounds of formula (I) are present in a greater amount, typically a much greater amount, than compounds of formula (Ia).

R and $R_1$ are predominately in the para- and para'-positions relative to the amino nitrogen. That is, the majority, e.g., greater than 50% by weight, such as 60% or more, 70% or more, or 80% or more by weight, of the di-alkylated diphenylamines of the inventive compositions are compounds of formula (I) wherein R and $R_1$ are on separate phenyl rings and para- to the amino group as in formula (II):

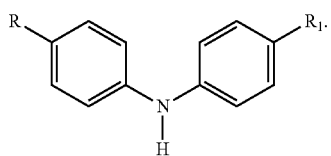

Often, more than one compound of formula (I), formula (Ia) and/or formula (II) are present.

In most embodiments of the invention, a portion of the compounds of the formulae (I), (Ia) and/or (II) will be compounds wherein $R_1$ is the same as R. For example, even in a process according to the invention wherein a reaction mixture comprising mono-alkylated diphenylamine and di-alkylated diphenylamine is reacted with a second olefinic agent selected to produce a di-alkylated compound wherein R and $R_1$ are different, the di-alkylated diphenylamine already present in the reaction mixture before the second olefin is added may be a compound of formula (I), (Ia) and/or (II) wherein R and $R_1$ are the same.

The composition provided by the invention comprises 15% or less, e.g., 10% or less and often 5% or less, by weight based on based on the on the total weight of substituted and unsubstituted diphenylamine compounds in the composition, of mono-alkylated diphenyl amine compounds, e.g., compounds of formula (III):

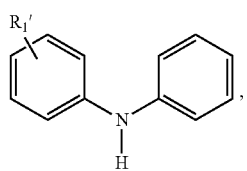

wherein, $R_1'$ is $C_{4-24}$ alkyl, e.g., $C_{8-24}$ alkyl, $C_{4-12}$ alkyl or $C_{8-12}$ alkyl, and more than one compound of formula (III) may be present. Typically, compounds of formula (III) with $R_1'$ in the para-position relative to nitrogen are present in greater amounts than compounds formula (III) where $R_1'$ is in an ortho or meta position.

Less than 2%, typically less than 1%, e.g. 0.5% or less, by weight based on the on the total weight of substituted and unsubstituted diphenylamine compounds in the composition, is unsubstituted diphenylamine. Polyalkylated diphenylamines such as tri-alkylated diphenylamines, tetra-alkylated diphenylamines and the like may also be present in minor amounts, e.g., less than 15 wt %, often than 10 wt %, typically less than 5 wt %.

Further, while the majority of diphenylamine compounds in the present diphenylamine compositions are di-alkylated diphenylamines bearing at least one alkyl group of 8-24 carbon atoms, it is possible in some embodiments that a minor portion of the composition, i.e., less than 30% wt %, e.g., less than 20 wt % often less than 10 wt % and typically less than 5 wt %, of the composition may comprise di-alkylated diphenyl amine compounds bearing two $C_{4-7}$ alkyl groups, depending on the identity of $R_1$ and the manner in which the diphenylamine is alkylated. However, di-$C_{4-7}$alkyl-diphenylamines are not preferred and in most embodiments are avoided, or kept to a minimum.

The composition of the invention is efficiently obtained by a process comprising a step wherein a mixture comprising mono-alkylated diphenylamine, di-alkylated diphenylamine, Lewis acid catalyst and a first olefinic agent present in a quantity sufficient to suppress dealkylation is reacted with a second olefinic agent in sufficient quantity to reduce the amount of mono-alkylated diphenylamine to about 15 wt % or less, e.g., 10 wt % or less often about 5 wt % or less of all diphenyl amine compounds, at which time the reaction may be worked up by standard means. Typically the alkyl groups of the mono-alkylated diphenylamine and di-alkylated diphenylamine in the mixture to which the second olefinic agent is added are selected from $C_{4-24}$ or $C_{8-24}$ alkyl. Volatile components of about 350 Daltons or less may be removed by distillation, vacuum distillation, sparging, or combinations thereof.

The first olefinic agent being "present in a quantity sufficient to suppress dealkylation" means that the first olefinic agent is present in an amount that will prevent or reduce to an acceptable level the loss of alkyl groups already present on the diphenylamine compounds prior to reaction with the second olefinic agent.

In many embodiments the second olefinic agent is added to a reaction mixture wherein the mono-alkylated diphenylamine is present in amounts of about 25 wt % or less based on the on the total weight of substituted and unsubstituted diphenylamine compounds in the mixture, and the majority other diphenylamine compounds in the reaction mixture are di-alkylated diphenyl amines. In some embodiments, 50 wt % or more, e.g., 55 wt % or more of this reaction mixture are di-alkylated diphenyl amines. Tri-alkylated and tetra-alkylated diphenylamines may also be present in the reaction mixture and other substituted diphenylamines may be present, but only in very minor amounts. For example, diphenylamines bearing three or more alkyl groups are typically less than 15, 10 or 5 wt % of diphenylamine compounds present in the reaction mixture prior to alkylation by the second olefinic agent. Non-alkylated diphenylamine, if present in the reaction mixture during alkylation by the second olefinic agent, is present at 6 wt % or less.

In many embodiments of the invention, the first and second olefinic agents comprise one or more compounds of the formula (IV)

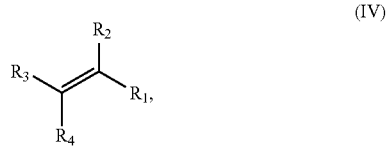

wherein

R$_1$ is C$_{1-22}$ straight chain alkyl or C$_{3-22}$ branched alkyl, and R$_2$, R$_3$ and R$_4$ are each independently selected from the group consisting of H, C$_{1-21}$ straight chain alkyl and C$_{3-21}$ branched alkyl. For example, in many embodiments R$_1$ is C$_{3-12}$ straight chain or branched alkyl, and R$_2$, R$_3$ and R$_4$ are each independently selected from the group consisting of H, C$_{1-12}$ straight chain alkyl or C$_{3-12}$ branched alkyl.

Typically at least one of R$_2$, R$_3$ and R$_4$ are straight chain or branched alkyl, e.g., in many embodiments R$_1$ is C$_{1-21}$ straight chain alkyl or C$_{3-21}$ branched alkyl, e.g., C$_{3-12}$ straight chain or branched alkyl, and R$_2$, R$_3$ and R$_4$ are each independently selected from the group consisting of H, C$_{1-21}$ straight chain alkyl and C$_{3-21}$ branched alkyl, e.g., H, C$_{1-10}$ straight chain alkyl and C$_{3-10}$ branched alkyl, wherein at least one of R$_2$, R$_3$ and R$_4$ are other than H.

In some embodiments, one or more olefinic agents comprise one or more compounds of formula (IV) wherein R$_3$ and R$_4$ are H and R$_2$ is straight chain or branched alkyl, e.g., compounds of formula (V)

(V)

wherein

R$_1$ is C$_{1-21}$ straight chain alkyl or C$_{3-21}$ branched alkyl, e.g., C$_{1-12}$ straight chain or branched alkyl and R$_2$ is C$_{1-21}$ straight chain alkyl or C$_{3-21}$ branched alkyl, e.g., C$_{1-10}$ straight chain alkyl or C$_{3-10}$ branched alkyl.

"Straight chain alkyl" is a linear alkyl group having a number of carbon atoms within the stated range, e.g., C$_{1-12}$ straight chain alkyl is selected from methyl, ethyl, n-propyl, n-butyl, n-pentyl, n-hexyl, n-heptyl, n-octyl, n-nonyl, n-decyl, n-undecyl, n-dodecyl.

"Branched alkyl" is an branched alkyl group having a number of carbon atoms within the stated range e.g., C$_{3-12}$ branched alkyl consists of branched isomers of C$_{3-12}$ straight chain alky such as 1-methylethyl (i.e., isopropyl), 1-methylpropyl, 2-methylpropyl, 1,1-dimethylethyl (i.e., tert-butyl), 1-methylbutyl, 2-methylbutyl, 3-methylbutyl, 1,1-dimethylpropyl, 1,2-dimethylpropyl, 2,2-dimethylpropyl, 1-ethylpropyl, 1,1-dimethylbutyl, 1,2-dimethylbutyl, 1,3-dimethylbutyl, 2,3-dimethylbutyl, 2-ethylhexyl, 1,3,5-trimethylhexyl and the like.

"Alkyl" without a further descriptor is a straight chain or branched alkyl having a number of carbon atoms within the stated range.

Commercially available olefins useful in olefinic agents in some embodiments of the invention include, for example, isobutylene, diisobutylene, high vinylidene propylene trimer (also known as highly reactive propylene trimer), propylene dimer, propylene trimer, propylene tetramer, propylene pentamer, 1-methylcyclohexene, isopentene, α-pinene, β-pinene, and α-methyl styrene.

In one embodiment, the composition is prepared by a process further comprising a first step for preparing the mixture of mono- and di-alkylated diphenyl amines which is subjected to alkylation by the second olefin, e.g., a process comprising, a) alkylating diphenylamine and/or a mono-alkylated diphenylamine of formula (III) above with a first olefinic agent in the presence of a Lewis acid catalyst to provide a reaction mixture comprising about 25% or less mono-alkylated diphenylamine and less than about 6% non-alkylated diphenylamine, based on the on the total weight of substituted and unsubstituted diphenylamine compounds in the reaction mixture, with the balance of diphenylamine compounds being predominantly di-alkyl diphenylamine, e.g., 50 wt %, 55 wt %, 60 wt % or more of all other diphenyl amine compounds in the reaction mixture are di-alkyl diphenylamines, as measured by, e.g., chromatography such as liquid or gas chromatography, or estimated from alkylation rates, b) adding additional first olefinic agent sufficient to suppress dealkylation, and c) adding a second olefinic agent in sufficient quantity to obtain a product mixture wherein the amount of monoalkylate is reduced to about 15% or less, e.g., 10% by weight or less often about 5% by weight or less, based on the total weight of substituted and unsubstituted diphenylamine compounds in the product mixture, at which time the reaction may be worked up by standard means. Volatile components of about 350 Daltons or less may be removed by distillation, vacuum distillation, sparging, or combinations thereof.

The first and second olefinic agents may comprise one or more than one olefin and in many embodiments comprise a branched olefin, for example a vinylidene compound, such as 2-ethyl-1-hexene; 2-methyl-1-undecene; 2,4,4-trimethyl-1-pentene (α-diisobutylene) and the like; trisubstituted olefins such as 2,4,4-trimethyl-2-pentene (β-diisobutylene); propylene trimer ("nonenes"), propylene tetramer, 1-methylcyclohexene, and the like; and tetrasubstituted olefins such as tetramethylethylene and the like. In general, vinylidenes, trisubstituted olefins and tetrasubstituted olefins exhibit a greater selectivity for para-substitution than linear olefins.

Steps b) and c) may be performed sequentially or together, i.e., step c) may be performed after step b) is performed, or the addition of step b) overlaps or occurs simultaneously with the addition of step c).

It is also possible that step a) and step b) can be carried out in an integrated manner, e.g., a process wherein the first olefinic agent is added to the starting diphenylamine and/or monoalkylated diphenylamine in an amount of first olefinic agent that is in excess of the amount needed to prepare the reaction mixture comprising di-alkyl diphenylamine, about 25% or less of mono-alkylated diphenylamine and less than about 6% non-alkylated diphenylamine. For example, in some embodiments the first olefinic agent is added to the starting diphenylamine and/or mono-alkylated diphenylamine gradually over time, or in portions, so that the final parts of the addition provides the additional amount of first olefinic agent sufficient to suppress dealkylation as called for in step b). Adding the amount of the first olefinic agent of steps a) and b) all at once is possible, but is generally not preferred.

In some embodiments, step a) of the process above comprises adding the first olefinic agent to a mixture comprising diphenylamine and Lewis acid catalyst. In some embodiments, step a) comprises adding the first olefinic agent to a mixture comprising mono-alkyl diphenylamine and Lewis acid catalyst. In other embodiments, step a) comprises adding the first olefinic agent to a mixture comprising both diphenylamine and mono-alkyl diphenylamine and Lewis acid catalyst.

In certain embodiments, step a) of the process above comprises adding the first olefinic agent to a mixture comprising a Lewis acid and a commercially obtained diphenylamine composition, or a diphenylamine composition prepared separately, which diphenylamine composition already contains di-alkylated diphenylamines e.g., 5 wt %, 10 wt %, 15 wt %, 20 wt % di-alkylated diphenylamines or more, and in some embodiments significant amounts e.g., 25 to 70 wt %, such as 30 to 65 wt %, of di-alkylated diphenylamines are present, based on the on the total weight of substituted and unsubstituted diphenylamine compounds in the starting diphenylamine composition, wherein the balance of diphenylamine compounds is mainly mono-alkylated diphenylamines.

It is understood by one skilled in the art that when adding a "first olefinic agent" to a diphenylamine composition already comprising mono-alkylated diphenylamine that the alkyl group of the mono-alkylated diphenyl amine is derivable from the first olefinic agent.

Examples of commercially available diphenylamine compositions include, e.g., Naugalube® 438, Naugalube® 438L, and Naugalube® AMS, available from Chemtura Corp.; Irganox® L01, Irganox® L57, and Irganox® L67 available from BASF; Vanlube® 81 and Vanlube® 961, available from R.T. Vanderbilt; Additin® RC 7001 and Additin® RC 7130 available from RheinChemie (Lanxess); Good-Rite® 3128 and Good-Rite® 3180 available from Emerald Performance Materials; and Westco® AO 445, available from Western Reserve Chemical.

Step a) can be obviated by obtaining or separately preparing an alkylated diphenylamine composition that already comprises di-alkyl diphenylamine and about 25% or less, e.g., 10 to 25%, or 15 to 25%, mono-alkylated diphenylamine and less than about 6%, e.g., 0 to 5%, non-alkylated diphenylamine. Adding a first olefinic agent sufficient to suppress dealkylation as in step b), adding a Lewis acid catalyst if needed, and adding a second olefinic agent as in step c) provides, after appropriate work-up, the liquid di-alkylated diphenylamine composition of the invention.

Obtaining or separately preparing an alkylated diphenylamine composition that contains di-alkylated diphenylamine, about 25% or less mono-alkylated diphenylamine and less than about 6% non-alkylated diphenylamine that also comprises an additional first olefinic agent sufficient to suppress dealkylation, obviates steps a and b). Addition of the second olefinic agent to this composition in the presence of a Lewis acid catalyst as in step c), typically followed by standard isolation or work-up procedures, provides the liquid di-alkylated diphenylamine composition of the invention.

The reactions in the present processes are Friedel-Crafts type reactions catalyzed by a Lewis acid. To be clear, as used herein, "a" or "an" can signify a single entity or more than one entity, e.g., "a Lewis acid catalyst" may one or more Lewis acids. A wide variety of Lewis acids are known to catalyze Friedel-Crafts reactions in general and the alkylation of diphenylamines specifically. For example, metal halides such as $AlCl_3$, $ZnCl_2$, $SnCl_4$, $BF_3$, $SbCl_3$ and the like, metal alkyls, alkylated metal halides, metal oxides, silicas, acid clays are some of the catalysts that have been used in Friedel-Crafts reactions, and any such catalyst known to catalyze olefin addition to aromatic amines may be adapted for use in the present invention.

The reactions may be run in the presence of an added organic solvent but can be efficiently run in the absence of an added solvent. Similar reactions in the art have used excess olefin as solvent and the same can be done here. Elevated reaction temperatures are also common in the practice of the present process as are increased pressures. For example, reaction temperatures of from 80 to 220° C. are common, e.g., from about 100 to about 200° C. depending on catalyst, alkylating agents and the presence of particular alkyl groups on the starting diphenyl amine. The exact conditions, e.g., temperature, concentrations of reaction components, pressure, and the like, are similar to those used in other similar Friedel-Crafts reactions and may be optimized through routine experimentation by one skilled in the art.

The olefins used for the first and second olefinic agent are well known. In some embodiments the olefins are derived from propene or isobutylene, e.g., the one or more olefins comprise one or more of isobutylene, diisobutylene, triisobutylene, tetraisobutylene, propylene dimer, propylene trimer, propylene tetramer, tetramethylethylene and the like. Often, the olefin will comprise mixtures of propylene oligomers or mixtures of butylene oligomers. For example, in some embodiments the first and/or second olefinic agent comprises propylene trimer, propylene tetramer, tetramethylethylene or diisobutylene; in some embodiments the first olefinic agent comprises propylene trimer or propylene tetramer; and in some embodiments the second olefinic agent comprises tetramethylethylene or diisobutylene.

Under the acidic conditions of the present alkylation process, a variety of reactions are known to occur. For example, the olefins used as alkylating agents may dimerize or trimerize etc., the position of the double bound may migrate, other isomerizations may take place, and olefins may crack to form smaller olefins. For example, diisobutylene is a well-known alkylating agent that under the reaction conditions can form isobutylene, which may then alkylate diphenylamine forming a butylated DPA adduct. Furthermore, alkyl groups already present on the phenyl ring may dealkylate and be replaced with a different alkyl groups from another olefin.

As is well known, regio-isomers on the phenyl rings, i.e., variations in the carbon of the phenyl that is alkylated, typically ortho- and para- to the amino group, are possible as are positional isomers of the alkyl groups, i.e., variations in the carbon of the alkyl group that is bound to the phenyl ring.

As a result of the possible cracking, rearrangement and scrambling of the olefinic agents and alkyl substituents that may occur under the reaction conditions of the invention, the alkyl group substituents of the diphenylamine product composition need not necessarily correlate exactly with the olefinic agents added to the reaction mixture. For example, reaction of nonyl diphenylamine with diisobutylene under Friedel-Crafts conditions can provide a mixture of compounds that may include di-alkylated compounds such as nonyl-octyl-diphenylamines, nonyl-butyl-diphenylamines, dinonyl-diphenylamines, di-octyl diphenylamines, di-butyl-diphenylamines, octyl-butyl-diphenylamines, etc., various mono-, tri- or tetra-alkylated compounds and minor amounts of non-alkylated material. Of course not all these compounds have an equal probability of forming.

The liquid alkylated diphenylamine compositions of the present invention typically comprise mixtures of diphenylamine compounds that may differ by the number of alkyl substituents on the phenyl rings, the position of the alkyl substituents on the phenyl rings and/or the chemical composition of the alkyl substituents, i.e., number of carbons and or the particular isomer of the alkyl substituents, wherein at least 70 wt %, typically 80 wt % or more, of all diphenylamine compounds in the composition are di-alkylated and over 50% of all di-alkylated diphenylamine compounds are 4,4'-di-alkylated diphenylamines.

For example, in many embodiments, the liquid, alkylated diphenylamine composition comprises, from about 70 to about 95, 99 or 100 wt %, e.g., from about 80 to about 95, 99 or 100 wt % di-alkylated diphenylamine compounds, wherein at least 55%, e.g., at least 60%, 65%, 70%, 75%, 80% or more, of the di-alkylated diphenylamine compounds are 4,4'-di-alkylated diphenylamine compounds, from 0 or 0.1 to 15 wt %, e.g., 0 or 0.1 to 5 wt %, mono-alkylated diphenylamine compounds, from 0 or 0.1 to 10 wt %, e.g., 0 or 0.1 to 5 wt %, tri-alkylated diphenylamine compounds, from 0 or 0.1 to 5 wt % tetra-alkylated diphenylamine compounds, and less than 2 wt %, e.g., 0.01 to 2 wt % or 0.01 to 2 wt %, non-alkylated diphenylamine.

In some embodiments the liquid, alkylated diphenylamine composition comprises, from about 80 to 100 wt %, e.g., about 85 to 100 wt % di-alkylated diphenylamine compounds, wherein at least 65%, 70%, 75%, 80%, 85% or more, of the di-alkylated diphenylamine compounds are 4,4'-di-alkylated diphenylamine compounds, from 0 or 0.1 to 10 wt %, e.g., 0 or 0.1 to 5 wt %, mono-alkylated diphenylamine compounds, from 0 or 0.1 to 10 wt %, e.g., 0 or 0.1 to 5 wt %, tri-alkylated and tetra-alkylated diphenylamine compounds, and less than 2 wt %, e.g., less than 1 wt %, e.g., less than 0.5 wt % or less than 0.1 wt %, non-alkylated diphenylamine.

Often, the composition of the invention comprises less than 5 wt % mono-alkylated diphenylamine compounds, e.g., 0 to 4.9 wt %, 0.01 to 4 wt % or 0.1 to 3 wt %. Often, the composition of the invention comprises less than 5 wt % tri-alkylated diphenylamine compounds, e.g., 0 to 4.9 wt %, 0.01 to 4 wt % or 0.1 to 3 wt %. Often, the liquid alkylated diphenylamine composition of the invention comprises 60 wt % or more, e.g., from about 65 wt %, 70 wt % or 75 wt % to about 95 wt % or 99 wt %, of 4,4'-di-alkylated diphenylamines of formula (II), based on the on the weight of substituted and unsubstituted diphenylamine compounds in the composition.

In certain embodiments neither of the first or second olefinic agents comprises styrene or styrene derivatives, such as alpha-methyl styrene. In certain embodiments the first olefinic agent as added does not comprise isobutylene and in some embodiments neither of the first or second olefinic agents as added comprises isobutylene. Given that under the reaction conditions of the invention isobutylene may form other olefins, e.g., diisobutylene, the term "as added" means that isobutylene is absent from the olefinic agent at the time of addition, or only a small amount of an isobutylene impurity, e.g., 10 wt %, 5 wt %, 2 wt % or less of the olefinic agent is present at the time of addition.

Preparing compositions rich in di-alkylated diphenylamines by the present process overcomes many of the drawbacks of other possible methods. It avoids the use of toxic aromatic alkylating agents such as styrene and avoids excessive or unwanted dealkylation of already alkylated diphenylamines. The use of unduly large excesses of olefinic alkylating agent and complications associated with the formation and removal of significant amounts of high molecular weight olefin oligomers are also avoided.

Further, the present alkylation method is shown to be high yielding and selective, forming high percentages of 4,4'-(i.e., para, para'-)substituted diphenylamines which obviates any need to enhance the amount of di-alkylated material by methods such as distillation, which can produce poor results and/or very low overall yields.

EXAMPLES

Examples 1, 2 and 3 are comparative examples outside of the present invention.

Example 1—Alkylation of 79%-Mono t-Octyl DPA with Nonenes

Diphenylamine was alkylated with 1.97 equivalents of diisobutylene at 130° C. in the presence of the acidified clay FILTROL 20X to yield after work-up a mixture comprising 79% mono-t-octyl DPA and 17% di-t-octyl DPA.

A 100 mL three neck flask (equipped with a spiral condenser with nitrogen inlet, overhead stirrer, and thermocouple) was charged with 10.28 grams of the 79% mono-t-octyl DPA above, 6.45 grams of a mixture of nonenes, and 0.514 g freshly crushed $AlCl_3$. The reaction was heated and stirred at 138° C. for 1 hour, then the reaction temperature was increased to 145° C. for 3 hours. An additional 4.4 g nonenes was added in three parts over the next 3.5 hours, the reaction temperature was reduced to 142° C. for 3.5 hours, an additional 0.77 grams of $AlCl_3$ was added and the reaction was stirred at 142° C. for an additional 8 hours. An additional 1.5 grams of nonenes was then added, and the reaction was stirred for an additional 1.5 h at 142° C. The reaction was worked up according to standard methods, washed, and concentrated using a rotary evaporator. The reaction was sparged at 0.22 torr to 220° C. to yield 9.09 grams of a dark green liquid containing, by gc analysis, 58% nonyl-octyl di-alkylated diphenylamine; 10% butyl-nonyl di-alkylated diphenylamine and 13% of what is believed to tri-alkylated DPA.

Example 2—Alkylation of Diphenylamine with Nonenes

Diphenylamine was alkylated with 6 equivalents of a mixture of nonenes 138° C. in the presence of $AlCl_3$ to yield after work-up a mixture containing, by gc analysis, 63% p,p'-dinonyl diphenylamine and 27% p-mononyl diphenylamine.

Example 3—Alkylation of Diphenylamine with Propylene Tetramer

A 100 mL three neck flask (equipped with an addition funnel with nitrogen inlet, overhead stirrer, and thermocouple) was charged with 14.39 grams of diphenylamine and 1.5 grams of freshly crushed $AlCl_3$. The addition funnel was charged with 42.42 grams of propylene tetramer. The reaction mixture was heated to 183° C., and the propylene tetramer was added slowly over the course of 5 hours. The reaction was stirred at 183° C. for an additional 5 hours. The reaction was worked up according to standard methods, washed, concentrated using a rotary evaporator and sparged at 0.61 torr to 220° C. to yield 24.37 grams of a dark amber liquid containing 39% didodecyl DPA, 32% mono-dodecyl DPA, and 23% tridodecyl DPA.

Example 4—Alkylation of Nonylated Diphenylamine with Tetramethylethylene and Nonenes A 50 mL three neck flask (equipped with a spiral condenser with nitrogen inlet, overhead stirrer mounted on top of a West condenser, and thermocouple) was charged with 10.71 grams of the commercially available NAUGALUBE 438L (i.e., a mixture comprising mono- and di-nonylated diphenylamine), 5.09 grams of a mixture of nonenes as the additional first olefinic agent, and 1.098 grams freshly crushed AlCl$_3$. Tetramethylethylene as second olefinic agent, 1.0 mL, was added, and the reaction was heated with stirring to 128° C. An additional 2.0 mL of tetramethylethylene was added in parts over 3 hours, maintaining a temperature of 120-128° C. The reaction was stirred at 128° C. for an additional 2 hours. The reaction was worked up according to standard methods, washed, and concentrated using a rotary evaporator to yield 10.92 grams of a clear, dark green liquid containing, by GC analysis, 76% dinonyl diphenylamine, 17% nonyl-(1,1,3-trimethylpropyl)diphenylamine, and 3% mononyl diphenylamine.

Example 5—Alkylation of Nonylated Diphenylamine with Diisobutylene and Nonenes In a manner similar to the procedure of Example 4, a mixture comprising NAUGALUBE 438L 2.3 equivalents of nonenes and AlCl$_3$ were mixed and heated to 134° C. while 2.9 equivalents of diisobutylene as second olefinic agent was added in parts to yield a product containing 49% of a mixture of dioctyl-, nonyl-octyl-, and di-nonyl diphenylamines; 34% of a mixture of butyl-octyl-, and butyl-nonyl-diphenylamines; and 10% of a mixture of mono-octyl diphenylamine and mono-nonyl diphenylamine.

Example 6—Sequential Alkylation of Diphenylamine with Propylene Tetramer and Diisobutylene A 100 mL three neck flask (equipped with an addition funnel with nitrogen inlet, overhead stirrer, and thermocouple) was charged with 15.47 grams of diphenylamine and 1.51 g freshly crushed AlCl$_3$. The mixture was heated to 184° C., and 23 grams propylene tetramer as first olefinic agent was added drop-wise from the addition funnel over 40 min. The latter part of the dropwise addition constituted adding additional first olefinic agent to suppress dealkylation. The reaction was stirred at 185-188° C. for 2.5 hours, cooled to 140° C. and 15.53 grams diisobutylene as second olefinic agent was added in three parts over 4 hours. The reaction was stirred at 141° C. for an additional 3 hours, worked up according to standard methods, washed, concentrated using a rotary evaporator and sparged at 0.65 torr to 152° C. Calcium carbonate was added and the reaction mass was sparged again at 0.56 torr to 261° C., then pressure filtered through Celite® 545 to yield 28.67 grams of a viscous amber liquid containing 56% didodecyl diphenylamine, 37% dioctyl diphenylamine and 7% butyl-octyl diphenylamine.

The amounts of di-alkylated, mono-alkylated and tri-alkylated diphenylamines of the examples above as determined by gas chromatography are compared in the following table.

|  | % Di-alkyl DPA | % Mono-alkyl DPA | % Tri-alkyl DPA |
|---|---|---|---|
| Ex 1 Comp | 68 | — | 13 |
| Ex 2 Comp | 63 | 27 | — |
| Ex 3 Comp | 39 | 32 | 23 |
| Ex 4 Inv | 93 | 3 | — |

-continued

|  | % Di-alkyl DPA | % Mono-alkyl DPA | % Tri-alkyl DPA |
|---|---|---|---|
| Ex 5 Inv | 83 | 10 | — |
| Ex 6 Inv | ~100 | — | — |

Samples of the of diphenylamine compositions from Ex. 1, 3, 4 and 6 were formulated into lubricating oils and tested for their performance in inhibiting oxidation induction via pressure differential scanning calorimetry (PDSC) techniques and deposit formation was measured via moderately high temperature thermo-oxidation engine oil simulation test (MHT TEOST). The results are found in the table below. Compositions according to the invention, Ex 4 and Ex 6, exhibit longer oxidation induction times (values are in minutes) and less deposits than either of the comparative Examples 1 and 3.

|  | % di-alkyl DPA | % Mono-alkyl DPA | % Tri-alkyl DPA | PDSC | MHT TEOST |
|---|---|---|---|---|---|
| Ex 1 Comp | 68 | — | 13 | 8.5 | 67.0 |
| Ex 3 Comp | 39 | 32 | 23 | 9.7 | 66.7 |
| Ex 4 Inv | 93 | 3 | — | 9.8 | 60.8 |
| Ex 6 Inv | ~100 | — | — | 11.1 | 61.8 |

What is claimed:

1. A process for preparing a liquid alkylated diphenylamine composition comprising from 80 to 100 wt % of one or more di-alkylated diphenylamines wherein more than 50 wt % of the di-alkylated diphenylamines are 4,4'-di-alkylated diphenylamines, 15 wt % or less of mono-alkylated diphenylamines, from 0 to 5 wt % tri-alkylated and tetra-alkylated diphenylamines, and less than 1 wt % unsubstituted diphenylamine, wherein each alkyl group is selected from C$_{4-24}$ alkyl and wherein at least one alkyl group of at least one di-alkylated diphenylamine contains from 8 to 24 carbon atoms, wherein in said process, to a reaction mixture comprising:

a di-alkylated diphenylamine, less than 25% by weight of mono-alkylated diphenylamine, less than 6% by weight of non-alkylated diphenylamine, Lewis acid catalyst comprising a metal halide, metal alkyl, alkylated metal halide, or acid clay, and a first olefinic agent to suppress dealkylation, which first olefinic agent is capable of producing the mono-alkylated diphenylamine and di-alkylated diphenylamine of the reaction mixture when reacted with diphenylamine in the presence of an acidic catalyst, wherein each wt % is based on the total weight of all substituted and unsubstituted diphenylamine compounds in the reaction mixture, and a majority of any other diphenylamine compounds are comprised of di-alkylated diphenylamine compounds, is added a second olefinic agent, which is chemically different from the first olefinic agent, comprising one or more compounds of formula (IV)

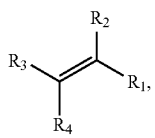

wherein
R$_1$ is C$_{1-21}$ straight chain alkyl or C$_{3-21}$ branched alkyl, R$_2$ is C$_{1-10}$ straight chain alkyl or C$_{3-10}$ branched alkyl, and R$_3$ and R$_4$ are each independently selected from the group consisting of H, C$_{1-10}$ straight chain alkyl and C$_{3-10}$ branched alkyl,
in sufficient quantity to reduce, upon reaction with the reaction mixture, the amount of mono-alkylated diphenylamine to 15 wt % or less of the total weight of substituted and unsubstituted diphenylamine compounds in the reaction mixture, wherein the alkyl groups of the mono-alkylated diphenylamine and di-alkylated diphenylamine in the mixture to which the second olefinic agent is added are selected from C$_{8-24}$ alkyl, and wherein neither of the first nor second olefinic agent as added comprises isobutylene, styrene or alpha-methyl styrene.

2. The process according to claim 1 for preparing a liquid alkylated diphenylamine composition wherein 80 wt % or more of the di-alkylated diphenylamines in the liquid alkylated diphenylamine composition are 4,4'-di-alkylated diphenylamines.

3. The process according to claim 1 wherein the Lewis acid catalyst comprises a metal halide.

4. The process according to claim 1 wherein the first olefinic agent and/or the second olefinic agent comprises more than one olefin.

5. The process according to claim 1 wherein the second olefinic agent comprises tetramethylethylene or diisobutylene.

6. The process according to claim 1 wherein the first olefinic agent comprises propylene trimer or propylene tetramer.

7. The process according to claim 1 comprising:
a) alkylating diphenylamine and/or mono-alkylated diphenylamine with a first olefinic agent in the presence of a Lewis acid catalyst comprising a metal halide, metal alkyl, alkylated metal halide, or acid clay, until less than 25% mono-alkylated diphenylamine and less than 6% non-alkylated diphenylamine remains, and a majority of any other diphenylamine compounds is comprised of di-alkylated diphenylamine compounds,
b) adding additional first olefinic agent in an amount sufficient to suppress dealkylation, and
c) adding the second olefinic agent, either after step b) or together with step b), in sufficient quantity to reduce the amount of mono-alkylated diphenylamine to 15% or less of the total weight of substituted and unsubstituted diphenylamine compounds in the reaction mixture.

8. The process according to claim 7 wherein the first olefinic agent comprises propylene trimer or propylene tetramer.

9. The process according to claim 7 wherein the second olefinic agent comprises tetramethylethylene or diisobutylene.

10. The process according to claim 7 wherein the Lewis acid catalyst comprises a metal halide.

11. The process according to claim 7 wherein the first olefinic agent and/or the second olefinic agent comprises more than one olefin.

* * * * *